United States Patent
Palanisamy et al.

(10) Patent No.: US 11,918,413 B2
(45) Date of Patent: Mar. 5, 2024

(54) ULTRASOUND PROBE, SYSTEM AND METHOD FOR MEASURING ARTERIAL PARAMETERS USING NON-IMAGING ULTRASOUND

(71) Applicant: KONINKLIJKE PHILIPS N.V., Eindhoven (NL)

(72) Inventors: Krishnamoorthy Palanisamy, Bangalore (IN); Rajendra Singh Sisodia, Bhopal (IN); Shriram Sethuraman, Lexington, MA (US); Ravindra Balasaheb Patil, Bangalore (IN); Vikram Basawaraj Patil Okaly, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 460 days.

(21) Appl. No.: 15/772,121

(22) PCT Filed: Nov. 2, 2016

(86) PCT No.: PCT/EP2016/076456
§ 371 (c)(1),
(2) Date: Apr. 30, 2018

(87) PCT Pub. No.: WO2017/076918
PCT Pub. Date: May 11, 2017

(65) Prior Publication Data
US 2019/0076113 A1 Mar. 14, 2019

Related U.S. Application Data

(60) Provisional application No. 62/249,989, filed on Nov. 3, 2015.

(51) Int. Cl.
*A61B 8/08* (2006.01)
*A61B 8/00* (2006.01)
*A61B 8/06* (2006.01)

(52) U.S. Cl.
CPC .............. *A61B 8/0891* (2013.01); *A61B 8/06* (2013.01); *A61B 8/4411* (2013.01);
(Continued)

(58) Field of Classification Search
CPC ....... A61B 8/0891; A61B 8/06; A61B 8/4411; A61B 8/4477; A61B 8/4494; A61B 8/488
See application file for complete search history.

(56) References Cited

U.S. PATENT DOCUMENTS

| 4,559,952 A | 12/1985 | Angelsen |
| 6,205,056 B1 | 3/2001 | Pan |

(Continued)

FOREIGN PATENT DOCUMENTS

| CN | 203724158 | 7/2014 |
| WO | 2007023426 A2 | 3/2007 |

(Continued)

OTHER PUBLICATIONS

Hoeks et al., Non-invasive measurement of mechanical properties of arteries in health and disease, Proceedings of the Institution of Mechanical Engineers, Part H: Journal of Engineering in Medicine 1999 213:3, 195-202, https://doi.org/10.1243/0954411991534924 (Year: 1999).*

(Continued)

*Primary Examiner* — John D Li (57) ABSTRACT

The invention relates to a system, an ultrasound probe and a corresponding method for measuring arterial parameters using non-imaging ultrasound. The system comprises an acquisition unit for acquiring doppler ultrasound signal from a blood vessel and a processing unit for processing the (Continued)

acquired doppler ultrasound signal and to determine the changes in the blood vessel through the measurements of at least Peak Systolic Velocity (PSV) and Pulse Wave Velocity (PWV). The acquisition unit comprises an ultrasound probe having a plurality of transducer elements arranged in a grid configuration, and comprising a first probe (102a) and a second probe (102b) detachably connected to each other. In the split configuration the ultrasound probe is provided to measure the PWV globally between the carotid and femoral arteries, or the PSV and PWV locally and simultaneously. In the integrated configuration the PSV or PWV may be measured locally.

12 Claims, 6 Drawing Sheets

(52) U.S. Cl.
CPC .......... *A61B 8/4477* (2013.01); *A61B 8/4494* (2013.01); *A61B 8/488* (2013.01)

(56) References Cited

U.S. PATENT DOCUMENTS

| | | | | |
|---|---|---|---|---|
| 2004/0088123 | A1* | 5/2004 | Ji | A61B 8/06 702/45 |
| 2005/0228416 | A1* | 10/2005 | Burbank | A61B 17/12 606/158 |
| 2006/0241427 | A1 | 10/2006 | Kinouchi | |
| 2007/0225606 | A1* | 9/2007 | Naghavi | A61B 5/022 600/438 |
| 2010/0049052 | A1* | 2/2010 | Sharf | G01S 7/52087 600/454 |
| 2012/0065514 | A1* | 3/2012 | Naghavi | A61B 5/6838 600/454 |
| 2014/0228688 | A1* | 8/2014 | Gupta | A61B 8/488 600/454 |
| 2014/0303501 | A1 | 10/2014 | Jin | |
| 2015/0080724 | A1* | 3/2015 | Rothberg | A61B 8/14 600/439 |

FOREIGN PATENT DOCUMENTS

| | | |
|---|---|---|
| WO | 2010/097728 | 9/2010 |
| WO | 2014/181961 | 11/2014 |
| WO | 2015/011594 | 1/2015 |
| WO | 2015026787 | 2/2015 |

OTHER PUBLICATIONS

R. B. Patil et al., "A method for localized computation of Pulse Wave Velocity in carotid structure," 2015 37th Annual International Conference of the IEEE Engineering in Medicine and Biology Society (EMBC), Milan, Italy, 2015, pp. 1898-1901, doi: 10.1109/EMBC.2015.7318753. (Year: 2015).*

Wang, et al., "Noninvasive Method for Measuring local Pulse Wave Velocity by Dual Pulse Wave Doppler: In Vitro and In Vivo Studies"; Plos One, vol. 10, No. 3, Mar. 18, 2015.

* cited by examiner

ULTRASOUND PROBE, SYSTEM AND METHOD FOR MEASURING ARTERIAL PARAMETERS USING NON-IMAGING ULTRASOUND

CROSS REFERENCE TO RELATED APPLICATIONS

This application is the U.S. National Phase application under 35 U.S.C. § 371 of International Application No. PCT/EP2016/076456, filed Nov. 2, 2016, published as WO 2017/076918 on May 11, 2017, which claims the benefit of U.S. Provisional Patent Application No. 62/249,989 filed Nov. 3, 2015. These applications are hereby incorporated by reference herein.

FIELD OF THE INVENTION

The invention relates to measuring the arterial parameters, more particularly to non-imaging and non-invasive mode of measuring the arterial parameters.

BACKGROUND

Atherosclerotic cardiovascular disease is one of the major causes of death in humans. An early detection of the atherosclerotic condition is very important in preventing certain cardiovascular events such as stroke, myocardial infarction etc. Studies have shown that the arterial stiffness and the measurement of the same, by detecting the changes in the vessel wall can be used as one of the primary parameter for the early detection of atherosclerotic cardiovascular disease, though the luminal narrowing may not be present at this stage. Changes in the vessel wall can be measured using the Pulse Wave Velocity (PWV), which is considered to be more reliable as compared to other techniques available for such measurements.

Currently, with the existing setup, PWV is measured between the carotid and femoral arteries thus making a global measurement that is non-imaging. However, localized measurement for the specific artery or the blood vessel renders the diagnosis more accurate. In this regard, localized measurement is done using imaging based ultrasound techniques. Also, in the non-imaging global measurement of the PWV, the carotid and femoral waves are normalized separately with the electrocardiogram (ECG) gating, since it is not possible to analyze these two waves simultaneously. In other words, the PWV measurement involves measurements from two locations of anatomical structures with gated ECG and the measured value is approximate as the exact distance between the carotid and femoral arteries varies from one subject to the other.

US2014303501A1 discloses two probes having different specifications for diagnosing a target object, and obtaining measurements thereof. Since, the probes has different specifications, their operating schema is also different, and hence may be required to synchronize with each other.

Therefore, there is a need for a localized PWV measurement using non-imaging ultrasound technique, and also capable of measuring the Peak Systolic Velocity (PSV) of carotid artery and PWV between carotid and femoral arteries besides measuring PWV of the carotid artery. The invention is aimed at overcoming the problem and providing a solution as stated herein before.

OBJECTS OF THE INVENTION

It is an object of the invention to provide a system that can measure the PWV locally at the carotid artery;

It is another object of the invention to provide a system that can measure the PSV locally at the carotid artery;

It is yet another object of the invention to provide a system that can measure the PWV between the carotid and femoral artery;

It is further object of the invention to provide a system that can measure the PWV and PSV using non-imaging ultrasound;

Another object of the invention is to provide a system that eliminates the need for normalizing the waves measured with the ECG gating;

Further object of the invention is to provide a method to measure the PSV and PWV locally at the carotid artery, and of the PWV between the carotid and femoral arteries using the system of the invention.

SUMMARY OF THE INVENTION

In one aspect of the invention, there is provided a system for measuring arterial parameters using non-imaging ultrasound. The system of the invention comprises an acquisition unit for acquiring doppler ultrasound signal from a blood vessel and a processing unit for processing the acquired doppler ultrasound signal and to determine the changes in the blood vessel through the measurements of at least Peak Systolic Velocity (PSV) and Pulse Wave Velocity (PWV). The acquisition unit comprises an ultrasound probe having a plurality of transducer elements arranged in a grid configuration, and comprising a first probe and a second probe detachably connected to each other.

It is advantageous to have an ultrasound probe that can be used in the measurement of PSV and PWV locally, and of the PWV globally, to enable improved diagnosis by detecting the changes in the blood vessel correlating to the stiffness in the blood vessel and of the early detection of atherosclerotic condition.

The invention provides a solution through a non-imaging and non-invasive system and method for measuring arterial parameters. The invention also provides an ultrasound probe that can be used in a split configuration and integrated configuration that enables it to measure the PSV and PWV locally and of the PWV globally.

In one preferred embodiment of the invention, a plurality of transducer elements are arranged in a grid configuration. The transducer elements are capable of being operated individually or collectively besides its capability of being used simultaneously or separately. The transducer elements may also be used in a non-phased manner.

In another aspect of the invention, there is provided an ultrasound probe for enabling the measurement of arterial parameters. The ultrasound probe of the invention has a plurality of transducer elements arranged in a grid configuration. The ultrasound probe has a first probe and a second probe that are detachably connected to each other. The ultrasound probe also has a latching mechanism to latch the first probe and the second probe to provide a single probe in an integrated configuration of the ultrasound probe, and to unlatch/detach the first probe and the second probe to provide two probes in a split configuration of the ultrasound probe.

In yet another aspect of the invention, there is provided a method for measuring arterial parameters using non-imaging ultrasound. The method of the invention comprises acquiring doppler ultrasound signal from a blood vessel by an acquisition unit having an ultrasound probe comprising a first probe and a second probe detachably connected to each other; and processing the acquired doppler ultrasound signal and determine the changes in the blood vessel through the measurements of at least Peak Systolic Velocity (PSV) and Pulse Wave Velocity (PWV), by a processing unit.

In one of the embodiment of the invention, the method of the invention is performed by the system of the invention using the ultrasound probe of the invention.

BRIEF DESCRIPTION OF THE DRAWINGS

With reference to the accompanying drawings in which.

DETAILED DESCRIPTION

Pulse Wave Velocity (PWV) is a measure of arterial stiffness or the rate at which pressure wave move down the blood vessel, and is a highly reliable prognostic parameter for cardiovascular morbidity and mortality. As blood flows through the blood vessels of the circulatory system, it moves out of the left ventricle and into the aorta where it is then pushed through the rest of the circulatory system. During systole, the contraction of the left ventricle and the ejection of blood into the ascending aorta acutely dilate the aortic wall and generate a pressure wave that moves along the arterial tree. The velocity of this movement gives a measurement of arterial compliance. With age or due to changes in the arterial wall, these blood vessels become stiffer and the speed at which the pressure wave moves through the system increases.

In addition to this, there are reflected pressure waves that move back towards the heart at the end of the systolic period. When the pressure waves move faster through the arteries, the reflected waves will also move back quicker. This causes more work on the cardiovascular system due to the increased afterload on the ventricle resulting in a greater systolic pressure needed to overcome this afterload. PWV is ideally computed by using two pressure catheters placed at a known distance from one another, referred to as the Pulse Wave Distance. The time it takes for the pressure wave to go from the upstream pressure catheter to the downstream pressure catheter provides the Pulse Transit Time (PTT). PWV can then be calculated by dividing the distance by the transit time providing a measure of cardiovascular health.

Among the different approaches currently available for evaluating arterial stiffness, the most widely used is the aortic pulse wave velocity, specifically in the area running from the aortic arch or common carotid artery to the common femoral artery. Typically, the pulse wave is detected by pressure transducers or arterial tonometry. The measurement of PWV between the carotid and femoral arteries is made by dividing the distance from the carotid point to the femoral point by the transit time.

Hence, $PWV = \frac{\Delta L (\text{meters})}{\Delta t (\text{seconds})}$

Transit time is estimated by the foot-to-foot method. The foot of the wave is defined at the end of diastole, when the steep rise of the waveform begins. The transit time is the time of travel of the foot of the wave over a known distance. Whereas the distance is a fixed parameter, the transit time has certain variability, depending on factors such as cardiac conduction and rhythm. Considering this, most methods take the average of several measurements. Although it is not possible to analyse the carotid and femoral waves simultaneously, it is normalized separately with the electrocardiogram (ECG) gating. A pulsed Doppler ultrasound with a Linear Array probe, synchronized with ECG and a minimum sliding window is used. The examination begins with the patient in a supine position after locating the carotid artery with B-mode at the supraclavicular level. Then the wave Doppler flow is identified simultaneously with ECG. The process is repeated on the common femoral artery in the groin. Each recording involves two or three cardiac cycles. To obtain the transit time (TT), it is measured from the R wave of QRS to the foot of the waveform using digital callipers.

The current approach described herein before has certain drawbacks that includes but not limited to obtaining measurements from two locations of anatomical structures with ECG gating and the measured value is approximate, as the exact distance between carotid and femoral arteries varies from subjects. Also, this provides the measurement of PWV globally and not of artery of interest locally. Besides this, an additional device such as ECG needs to be interfaced to obtain the transit time.

The invention provides a system and a method for measuring arterial parameters like PWV and PSV using a non-imaging and non-invasive based approach, locally and globally without ECG gating.

The invention is further described hereinafter with reference to FIGS. 1 to 6 through non-exhaustive exemplary embodiments.

Figure 1:
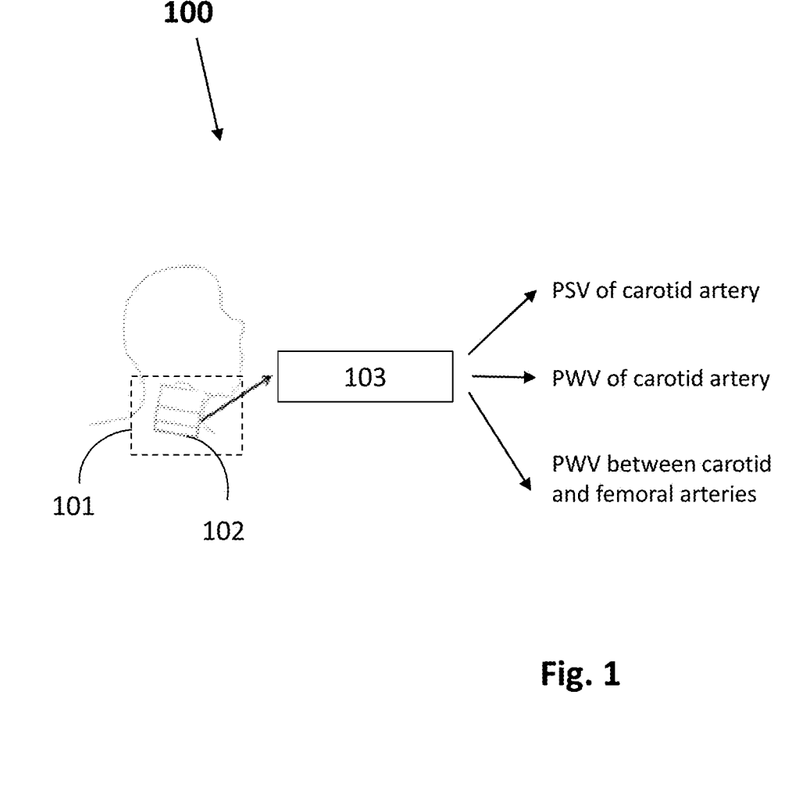
FIG. 1 shows a system for measuring arterial parameters, in accordance with the invention.
Figure 2A:
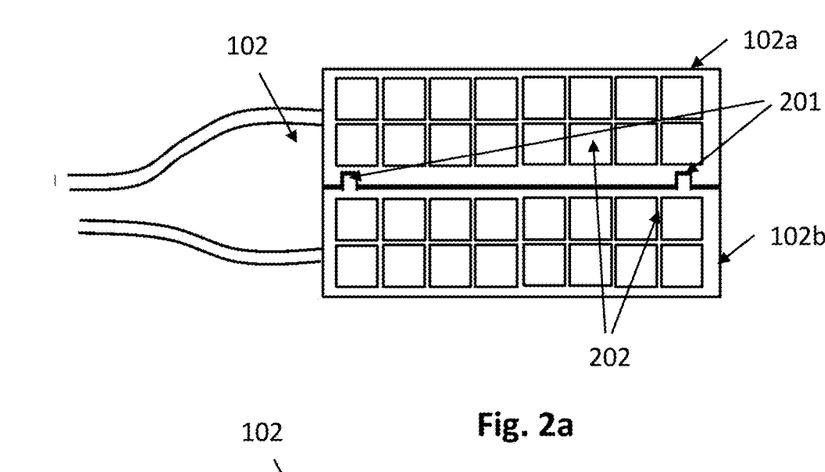
FIGS. 2a and 2b show an ultrasound probe in integrated configuration and split configuration, respectively.
Figure 2B:
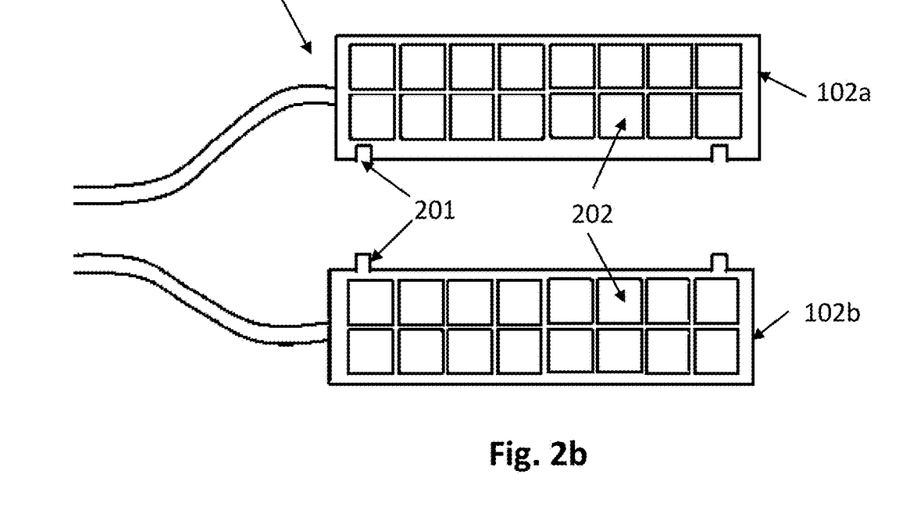
Figure 3A:
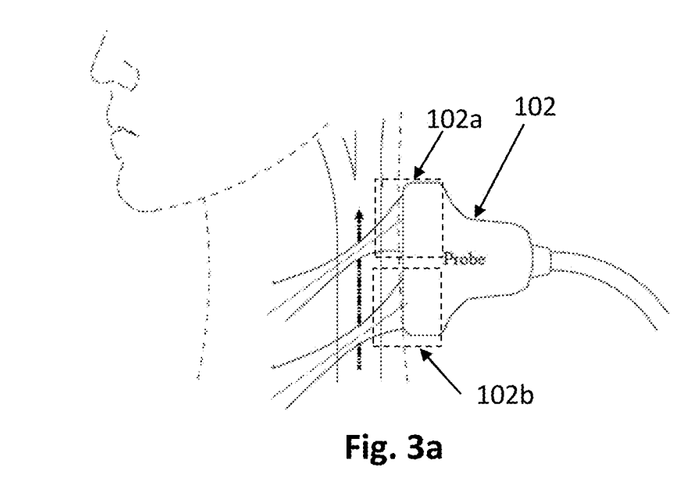
FIGS. 3a and 3b illustrates a set up measuring PWV and Doppler ultrasound acquired at two different locations, respectively.
Figure 3B:
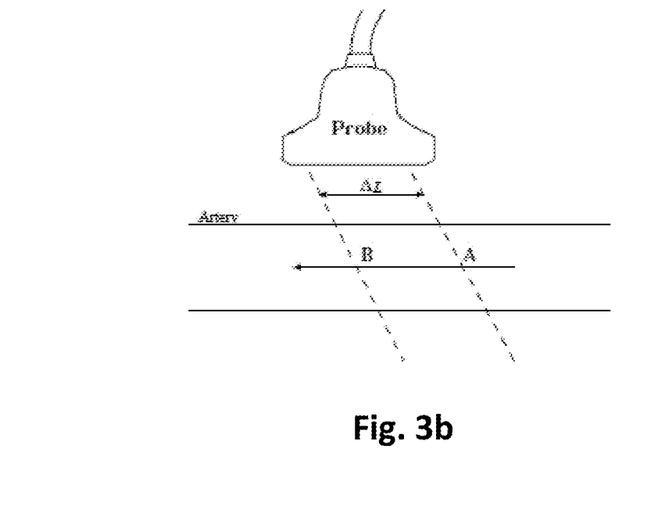
Figure 6:
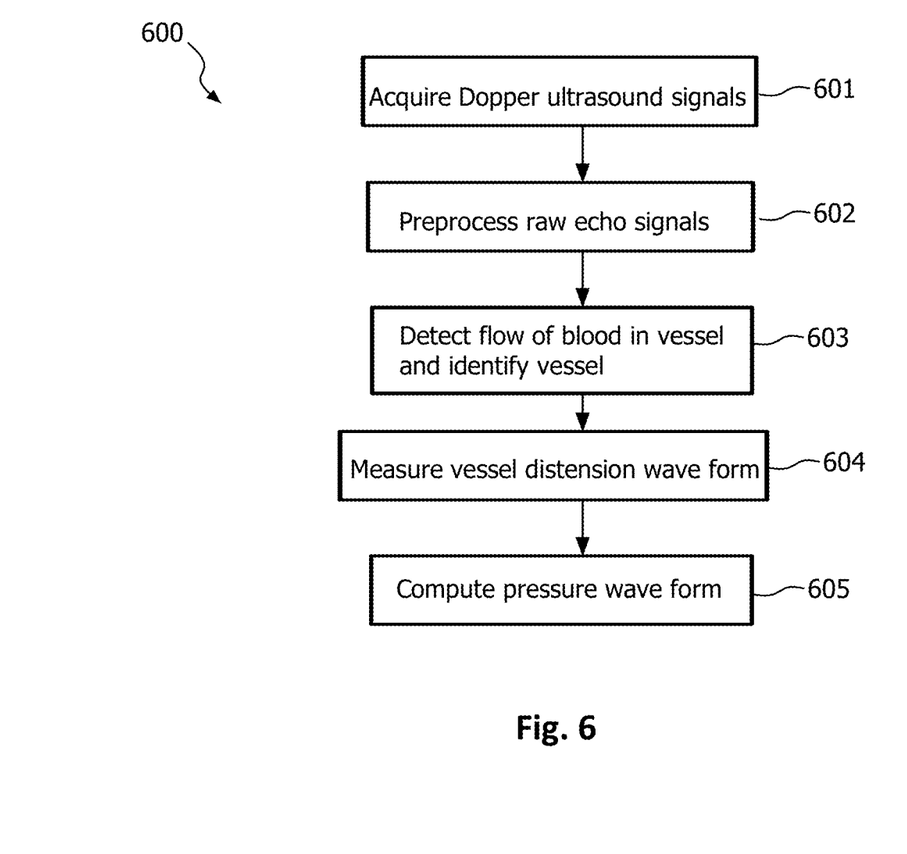
FIG. 6 shows a method of measuring arterial parameters, in accordance with the invention.

In FIGS. 1 and 6, a system (100) and a method (600) for measuring arterial parameters is shown. The system (100) comprises an acquisition unit (101) for acquiring Doppler ultrasound signals from a blood vessel, in accordance with the method step (601). The acquisition unit (101) has an ultrasound probe (102) having a plurality of transducer elements arranged in a grid configuration. The ultrasound probe (102) has a first probe and a second probe detachably connected to each other. As shown in FIG. 2a, a latching mechanism (201) is provided to latch the first probe (102a) and the second probe (102b) to provide a single probe in an integrated configuration of the ultrasound probe (102). In FIG. 2b, the latching mechanism (201) is shown in a detached manner to provide two probes namely, the first probe (102a) and the second probe (102b) detached from each other in a split configuration of the ultrasound probe (102). The transducer elements (202) of the ultrasound probe (102) are provided to operate individually or collectively, and may also be operated simultaneously or separately, in a non-phased manner. Also, the transducer elements of the ultrasound probe (102) are provided to produce collimated beam in a region of interest. As shown in FIG. 3a the ultrasound probe (102) is used in a split configuration with split probes (102a and 102b) to obtain PWV measurement locally, in accordance with one preferred embodiment of the invention. Doppler ultrasound waves are obtained from two different locations A and B in an artery, as shown in FIG. 3b. The Doppler ultrasound waveforms in first row and nth row of the transducer elements arranged in a grid will have time-shift with respect to each other. If, it is acquired simultaneously, this shift is related to the time taken for the cardiac pulse wave to travel cross the blood vessel from first row to the nth row. The time delay (D) between the two signals is computed from the Doppler ultrasound signal obtained from the locations A and B, where the A and B are located apart at a distance L. The PWV is estimated as follows:

$$PWV = \frac{L}{D}$$

Figure 4:
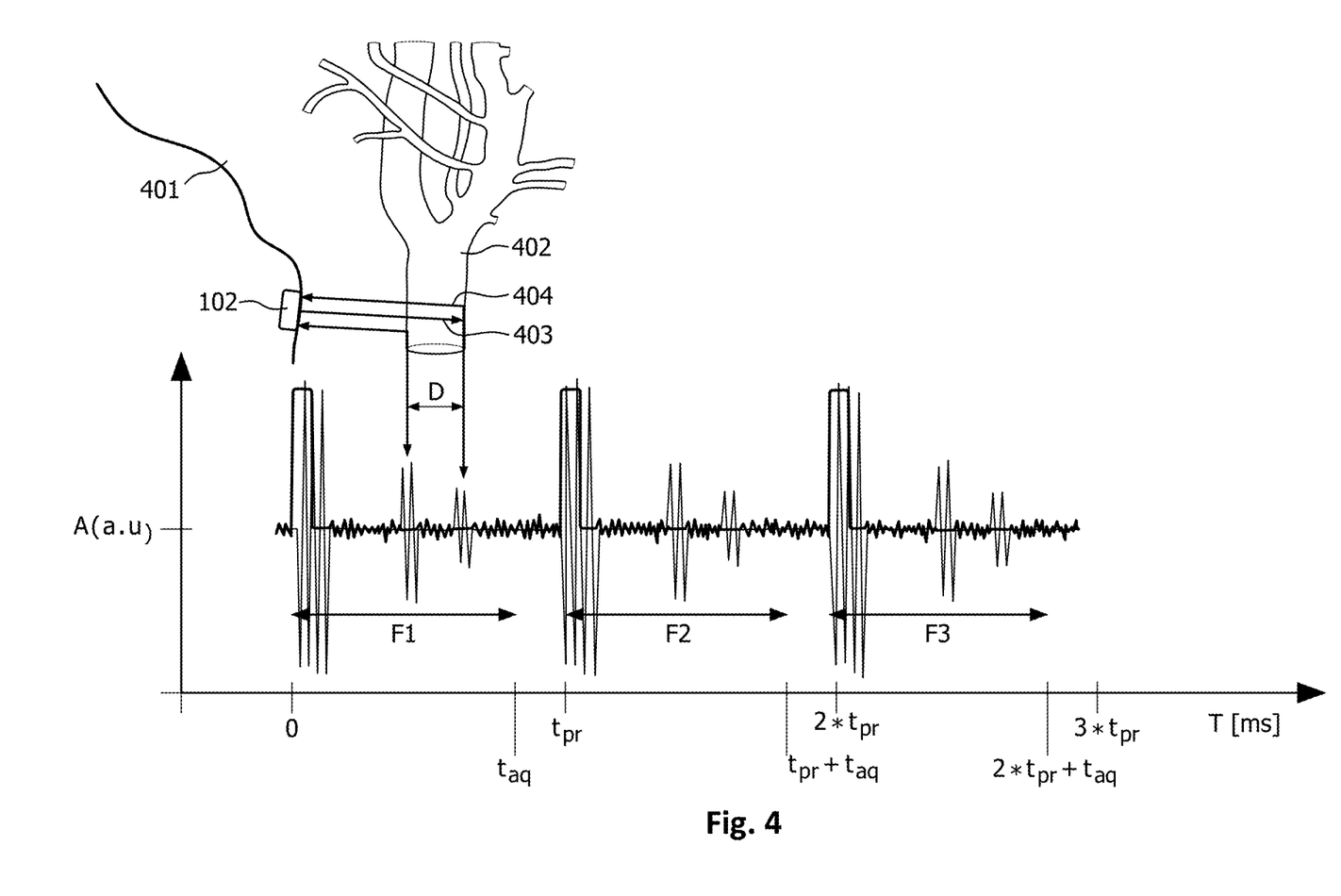
FIG. 4 illustrates the acquisition of doppler ultrasound information from an artery of interest.

The signal frames of the Doppler ultrasound signal are obtained over a particular interval of time as shown in FIG. 4, in respect of the blood vessel or artery of interest. The ultrasound probe (102) placed on the surface of the body sends ultrasound pulses into the body passing through the soft tissues (401) to reach the artery (402) like carotid artery. The ultrasound sound pulses (403) from the ultrasound probe (102) is shown reaching the farther wall of the artery (402) and the same been reflected. The reflected ultrasound pulse is shown as (404). Apparently, the ultrasound pulses are transmitted and the same gets reflected from the near, as well as far walls of the artery whose diameter is D. The echoes are received by the same ultrasound probe (102). The data frame (F1, F2 and F3) containing amplitude information A (a, u) formed over time interval T (ms), of the reflected echoes are shown. The diameter of the blood vessel or the artery is estimated in terms of the difference between the times of arrival of the two echoes (Δt) scaled by the sound velocity (v) as follows:

Diameter $D = 0.5 \times \Delta t \times v$

Figure 5:
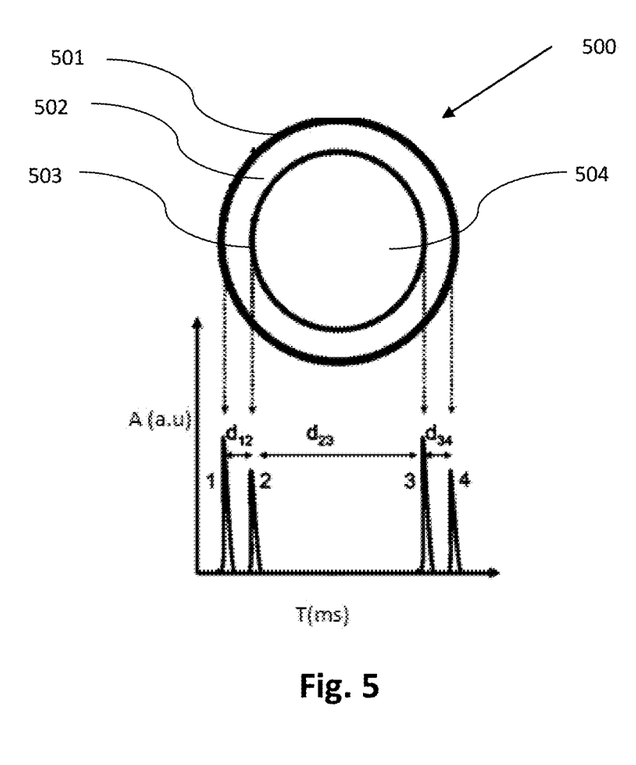
FIG. 5 depicts the echo pattern obtained at different part of an artery of interest.

FIG. 5 shows the echo patterns (1, 2, 3, 4) after the ultrasound waves gets reflected from the different anatomical site such as adventitia (501), media (502) and intima (503) of the blood vessel or artery (500) of interest. The transition from the inner layer of the wall (503), intima, to the cavity inside the artery, lumen (504) produces a distinct echo, visible both at the near wall and the far wall. A stronger echo represents the outermost layer, the adventitia (501). The middle layer, media (502), is hypo-echoic. Different echo pattern that are obtained and succeeding the gates are tracked based on the threshold to determine the anatomical structure from which it is reflected.

Echo pattern obtained is used to compute the distension waveform as it could be observed that the echo's obtained from an artery over the different regions as shown in FIG. 5 is not uniform.

The signal obtained from the ultrasound probe is affected with noise and transient behavior. The raw echo signals are preprocessed, in accordance with the method step (602) to improve SNR and the transients are removed by using matched filter followed by each row of RF data is filtered with band pass filter. Then a non-linear gain is applied to suppress high amplitude reflections from skin gel interface.

Then, the envelope e(t) of the gain compensated signal x(t) is calculated using Hilbert transform.

$$e(t) = \sqrt{x(t)^2 + H\{x(t)\}^2}$$

where $$H[x(t)] = \int_{\infty}^{\infty} \frac{x(\tau) d\tau}{t - \tau}$$

In method step (603), the processing unit detects the flow of blood in a blood vessel and identifies the blood vessel or the artery. Accordingly, the far wall and the near wall of an artery can be separated by performing the echo gate tracking. The echoes are identified to find the region of interest in acquired signals where the anatomical structure of an artery could be located. To identify the region of interest from an echo pattern, a probabilistic approach such as Maximum Likelihood approach is used. Firstly, the energy plot for the given signal is obtained using sliding window approach and regions of maximum energy are identified and various features are extracted from these regions of interest for different patients across frames. The feature data is trained using a Gaussian mixture model by obtaining mean and covariance. On providing a test frame, features are extracted and tested against the model built to provide the likelihood of region of interests. The data are classified based on a single class approach such as wall class approach. The method uses a cut-off value of likelihood to assign points to wall class.

$$P\left(\frac{x}{C}\right) = \frac{1}{2\pi^{\frac{d}{2}} (\det(c))^{0.5}} e^{-(x-\mu)^T C^{-1}(x-\mu)}$$

where, $d$- dimension of feature vector $c$- covariance matrix $\mu$- mean of Gaussian $x$- feature vector for test point The artery of interest, so identified is mapped to RF data for computation of artery specific distension waveform. The distension waveform of the blood vessel or the artery can be measured by continuously tracking the movement of the echoes coming from the walls of the blood vessel or the artery, in accordance with the method step (604).

Further, the variation of the blood flow during systolic and diastolic causes the change in the elastic property of an artery. This change in elastic property is manifested in diameter change of the artery. Based on the echoes obtained due to wall motion, successive signal frames are analyzed, and the distension waveform of the artery is computed as the difference between the near and far wall movements.

Considering the echoes obtained in two successive acquisitions, $NW_i(t)$ be the near wall echo and $FW_i(t)$ be the far wall echo in the $i^{th}$ acquisition. Now, the near and far wall echoes obtained in the next iteration may be expressed as $NW_{i+1}(t) = NW_i(t \pm \Gamma_{nw})$ $FW_{i+1}(t) = FW_i(t \pm \Gamma_{fw})$ where $\Gamma_{fw}$ and $\Gamma_{nw}$ are the shifts in the near and far wall echoes, respectively. Echo tracking involves estimating these shifts and following the movement of the echoes accordingly. To estimate the time shift of the echoes in between successive acquisitions, a shift and search approach is employed, and is ideal to compute the maximum cross correlation between the signals $NW_i(t)$ and $NW_{i+1}(t)$ and estimating the shift $\Gamma_{fw}$ and $\Gamma_{nw}$ as the time corresponding to maximum of the cross correlation.

Once the delay is identified, the wall movements are computed based on the sound velocity (v)

$d_{nw}(i) = 0.5 * v * [\Gamma_{nw}(i) + \Gamma_{nw}(i-1)]$ $d_{fw}(i) = 0.5 * v * [\Gamma_{fw}(i) + \Gamma_{fw}(i-1)]$ The artery distension waveform is computed as the difference between the near wall and far wall movements and is given by $$\Delta d(i) = d_{fw}(i) d_{nw}(i)$$

Substituting t=(i/fprf), the distension waveform Δd(t) can be determined as follows $$\Delta d(t) = d_{fw}(t) - d_{nw}(t)$$

From the above mentioned distension waveform, peak to peak distension can be computed, which can be used to measure other arterial compliance measure.

The pressure change in an artery is manifested better, by the change in cross section of an artery. Arterial wall cross-section as function of time is further computed based on distension waveform by the following equation.

$$A(t) = \frac{\pi d(t)^2}{4}$$

The functional relationship between the blood pressure waveform p(t) and arterial wall cross section A(t) is established as follows $$p(t) = p_o e^{\gamma A(t)}$$

Where $p_o$ is constant and γ varies between arteries of a patient and across patients. A look up table and arterial model is required to measure respective γ for the artery of interest.

From the equation $p(t)=p_o e^{\gamma A(t)}$, the pressure wave form can be computed, in accordance with method step (605). Also, systolic, diastolic and mean arterial pressure could therefore be estimated. It is hereby possible to continuously monitor the blood pressure for an artery of interest in non-invasive and non-imaging based approach.

As the change in diameter and the pressure associated with artery of interest are available, other arterial compliance measures such as Elastic modulus, Arterial distensibility, Arterial compliance and Stiffness index can be computed as below, where $P_s$ is systolic and $P_d$ is diastolic pressure.

$$\text{Elastic modulus, } E = \frac{\Delta P \times D}{\Delta D}$$

$$\text{Arterial Distensibility, } D = \frac{\Delta D}{\Delta P \times D_d}$$

$$\text{Arterial Compliance, } C = \frac{\Delta D}{\Delta P}$$

$$\text{Stiffness index, } \varphi = \frac{\ln(P_s/P_d)}{\left(\frac{D_s - D_d}{D_d}\right)}$$

The invention therefore provides continuous measurement of localized blood pressure of the artery of interest along with other arterial parameters and arterial compliance measures.

Only certain features of the invention have been specifically illustrated and described herein, and many modifications and changes will occur to those skilled in the art. The invention is not restricted by the preferred embodiment described herein in the description. It is to be noted that the invention is explained by way of exemplary embodiment and is neither exhaustive nor limiting. Certain aspects of the invention that not been elaborated herein in the description are well understood by one skilled in the art. Also, the terms relating to singular form used herein in the description also include its plurality and vice versa, wherever applicable. Any relevant modification or variation, which is not described specifically in the specification are in fact to be construed of being well within the scope of the invention. The appended claims are intended to cover all such modifications and changes which fall within the spirit of the invention.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

We claim:

1. A system for measuring arterial parameters using non-imaging ultrasound, the system comprising:
   an acquisition unit for acquiring Doppler ultrasound signals from at least one blood vessel, wherein the acquisition unit comprises an ultrasound probe having a plurality of transducer elements arranged in a grid configuration, the ultrasound probe having a first non-imaging ultrasound probe and a second non-imaging ultrasound probe detachably connected to each other, wherein the ultrasound probe is configured to provide a single non-imaging ultrasound probe in an integrated configuration of the ultrasound probe, and the ultrasound probe is configured to provide two non-imaging ultrasound probes in a split configuration of the ultrasound probe, wherein the first non-imaging ultrasound probe in the split configuration is positioned to acquire a first Doppler signal and the second non-imaging ultrasound probe in the split configuration is positioned to acquire a second Doppler signal originating from a different location in a body than the first Doppler signal; and
   a processing unit for processing the acquired Doppler ultrasound signals to determine a Pulse Wave Velocity (PWV) for the at least one blood vessel;
   wherein the processing unit is configured to calculate a global PWV for the at least one blood vessel when the ultrasound probe is in the split configuration, and a local PWV when the ultrasound is in the integrated configuration;
   wherein, when the ultrasound probe is in the split configuration, the processing unit is configured to calculate the global PWV for the at least one blood vessel based on a time delay between the first Doppler signal and the second Doppler signal; and
   wherein, when the ultrasound probe is in the integrated configuration, the processing unit is configured to: determine a distension waveform indicative of (i) differences between the movements of a near wall and a far wall of the at least one blood vessel, and (ii) changes in the cross section of the at least one blood vessel, and is further configured to determine a pressure wave form based, at least partially, on the distension waveform, and determine a local PWV based using the pressure wave form.

2. The system as claimed in claim 1, wherein the ultrasound probe has a latching mechanism to latch the first non-imaging ultrasound probe and the second non-imaging ultrasound probe to provide a single probe in the integrated configuration of the ultrasound probe, and to unlatch/detach the first non-imaging ultrasound probe and the second non-imaging ultrasound probe to provide two probes in the split configuration of the ultrasound probe.

3. The system as claimed in claim 1, wherein the transducer elements of the ultrasound probe are provided to operate individually or collectively.

4. The system as claimed in claim 3, wherein the transducer elements of the ultrasound probe are arranged to provide a collimated beam in a region of interest.

5. The system as claimed in claim 1, wherein the transducer elements of the ultrasound probe are provided to operate simultaneously or separately.

6. The system as claimed in claim 1, wherein the processing unit is provided to detect a flow of blood in the blood vessel.

7. The system as claimed in claim 6, wherein the processing unit is configured to identify a transducer element from the plurality of transducer elements and the blood vessel from which the flow of blood has been detected.

8. The system as claimed in claim 1, wherein when the ultrasound probe is in the split configuration, the processing unit is configured to simultaneously calculate a Pulse Wave Velocity using the first Doppler signal and a Peak Systolic Velocity using the second Doppler signal.

9. A method for measuring arterial parameters using non-imaging ultrasound, the method comprising:
acquiring Doppler ultrasound signals from at least one blood vessel by an acquisition unit having an ultrasound probe comprising a plurality of transducer elements arranged in a grid configuration, the ultrasound probe having a first non-imaging ultrasound probe and a second non-imaging ultrasound probe detachably connected to each other, wherein the ultrasound probe is configured to provide a single probe in an integrated configuration of the ultrasound probe, and the ultrasound probe is further configured to provide two non-imaging ultrasound probes in a split configuration of the ultrasound probe, and wherein when in the split configuration, acquiring Doppler ultrasound signals includes acquiring a first Doppler signal with the first non-imaging ultrasound probe and acquiring a second Doppler signal with the second non-imaging ultrasound probe, said second Doppler signal originating from a different location in a body than the first Doppler signal; and
processing the acquired Doppler ultrasound signals and determining a Pulse Wave Velocity (PWV) for the at least one blood vessel;
wherein processing the acquired Doppler ultrasound signals involves calculating a global PWV for the at least one blood vessel when the ultrasound probe is in the split configuration, and a local PWV when the ultrasound is in the integrated configuration;
wherein, when the ultrasound probe is in the split configuration, processing the acquired Doppler ultrasound signals further involves calculating the global PWV for the at least one blood vessel based on a time delay between the first Doppler signal and the second Doppler signal; and
wherein, when the ultrasound probe is in the integrated configuration, processing the acquired Doppler ultrasound signals further involves determining a distension waveform indicative of (i) differences between the movements of a near wall and a far wall of the at least one blood vessel, and (ii) changes in the cross section of the at least one blood vessel, and further involves determining a pressure wave form based, at least partially, on the distension waveform, and determining a local PWV based using the pressure wave form.

10. The method as claimed in claim 9, wherein the processing includes detecting the flow of blood in the blood vessel.

11. The method as claimed in claim 10, wherein the processing includes identifying a transducer element from the plurality of transducer elements and the blood vessel from which the flow of blood has been detected.

12. The method as claimed in claim 9, wherein when the ultrasound probe is in the split configuration, processing the acquired Doppler ultrasound signals further involves simultaneously calculating a Pulse Wave Velocity using the first Doppler signal and a Peak Systolic Velocity using the second Doppler signal.

* * * * *